US 9,364,841 B2

(12) United States Patent
Dunne et al.

(10) Patent No.: US 9,364,841 B2
(45) Date of Patent: Jun. 14, 2016

(54) CARTRIDGE SYSTEM

(75) Inventors: Stephen T. Dunne, Suffolk (GB);
Heinrich Kladders, Muelheim-Ruhr (DE)

(73) Assignee: BOEHRINGER INGELHEIM PHARMA GMBH & CO. KG, Ingelheim am Rhein (DE)

( * ) Notice: Subject to any disclaimer, the term of this patent is extended or adjusted under 35 U.S.C. 154(b) by 1638 days.

(21) Appl. No.: 12/864,944

(22) PCT Filed: Feb. 18, 2009

(86) PCT No.: PCT/EP2009/001153
§ 371 (c)(1),
(2), (4) Date: Jan. 10, 2011

(87) PCT Pub. No.: WO2009/103510
PCT Pub. Date: Aug. 27, 2009

(65) Prior Publication Data
US 2011/0168175 A1 Jul. 14, 2011

(30) Foreign Application Priority Data

| Feb. 19, 2008 | (GB) | 0802954.8 |
| Feb. 26, 2008 | (GB) | 0803403.5 |
| May 28, 2008 | (GB) | 0809602.6 |
| Jun. 10, 2008 | (GB) | 0810588.4 |

(51) Int. Cl.
*A61M 11/00* (2006.01)
*B05B 11/00* (2006.01)
(Continued)

(52) U.S. Cl.
CPC .......... *B05B 11/0054* (2013.01); *A61M 11/02* (2013.01); *A61M 15/0035* (2014.02); *B05B 11/0043* (2013.01); *B05B 11/0097* (2013.01);
(Continued)

(58) Field of Classification Search
CPC ............ A61M 15/00; A61M 15/0001; A61M 15/009; A61M 15/0086; A61M 16/0057; A61M 11/02; A61M 15/0035; B05B 11/0054; B05B 11/004; B05B 11/0043; B05B 11/0097; B05B 11/309; B65D 83/42; B65D 83/425; B65D 83/62
USPC ............. 128/200.14, 200.18, 200.21–200.23, 128/200.15
See application file for complete search history.

(56) References Cited

U.S. PATENT DOCUMENTS 3,933,279 A * 1/1976 Maier .......................... 222/631
3,951,310 A * 4/1976 Steiman ......................... 222/95
(Continued)

FOREIGN PATENT DOCUMENTS

| EP | 1312418 A2 | 5/2003 |
| EP | 1375385 A2 | 1/2004 |

(Continued)

OTHER PUBLICATIONS

International Search Report, Form PCT/ISA/210, for corresponding PCT/EP2009/001153; date of mailing: May 20, 2009.

*Primary Examiner* — Steven Douglas
(74) *Attorney, Agent, or Firm* — Michael P. Morris; Mary-Ellen M. Devlin

(57) ABSTRACT

An inhaler including a pre-inserted cartridge (100) is proposed. The cartridge contains liquid (103) which is preferably pressurized to a low pressure. The cartridge is connected via an aerosol valve (106) with the inhaler. The liquid is further pressurized by a pump (117) of the inhaler to a high pressure and atomized.

28 Claims, 10 Drawing Sheets

Figure 1:
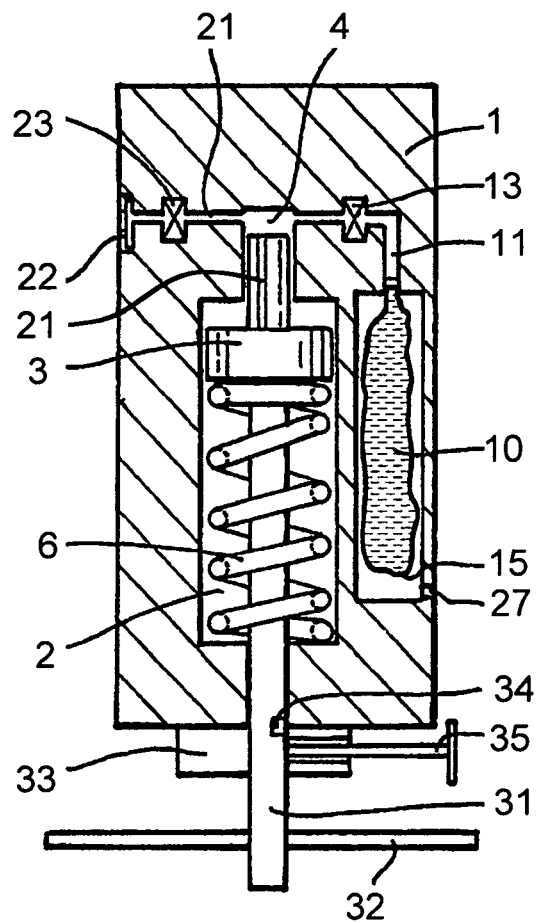

(51) Int. Cl.
*A61M 11/02* (2006.01)
*B65D 83/42* (2006.01)
*B65D 83/62* (2006.01)
*A61M 15/00* (2006.01)

(52) U.S. Cl.
CPC ............... *B65D 83/42* (2013.01); *B65D 83/62* (2013.01); *B05B 11/004* (2013.01); *B05B 11/309* (2013.01); *B65D 83/425* (2013.01)

(56) References Cited

U.S. PATENT DOCUMENTS

| | | | | |
|---|---|---|---|---|
| 4,067,499 | A * | 1/1978 | Cohen | 239/323 |
| 4,245,788 | A | 1/1981 | Wright | |
| 4,964,540 | A * | 10/1990 | Katz | 222/95 |
| 5,282,549 | A * | 2/1994 | Scholz et al. | 222/95 |
| 5,662,271 | A * | 9/1997 | Weston et al. | 239/321 |
| 6,464,108 | B2 * | 10/2002 | Corba | 222/136 |
| 6,789,702 | B2 * | 9/2004 | O'Connor et al. | 222/96 |
| 8,479,725 | B2 * | 7/2013 | Hausmann et al. | 128/200.14 |
| 8,734,392 | B2 * | 5/2014 | Stadelhofer | 604/124 |
| 2003/0209238 | A1 | 11/2003 | Peters et al. | |

FOREIGN PATENT DOCUMENTS

| | | |
|---|---|---|
| EP | 1595822 A1 | 11/2005 |
| EP | 1813548 A1 | 8/2007 |
| WO | 2004062813 A1 | 7/2004 |

* cited by examiner

CARTRIDGE SYSTEM

The present invention relates to a device, in particular for dispensing or atomizing a liquid, preferably an inhaler, with a preferably pre-inserted cartridge, to a method for filling such a cartridge with liquid, and to the use of such a cartridge for an inhaler.

The present invention relates in particular to the dispensing of a liquid which consists of or contains a medicament, a drug formulation or an inhalation formulation. The liquid is preferably atomized or dispensed as a spray or aerosol by means of a device, such as an inhaler or the like. Preferably, the cartridge forms a reservoir of the inhaler for multiple doses of the liquid and the inhaler comprises a pump for pressurizing one dose after the other taken from the cartridge and for discharging the respective dose of liquid in particular via a nozzle to atomize the liquid to form the spray or aerosol.

U.S. Pat. No. 5,662,271 A and GB U.S. Pat. No. 2,251,898 A describe a gas-free metered dose inhaler comprising a piston and cylinder arrangement where a liquid drug is pressurized and forced through an atomizing nozzle at high pressure. The inhaler further includes a non-return valve connecting the cylinder to a container for storing the liquid drug. Three types of containers are described, namely a collapsible bag, a spring-loaded piston and cylinder arrangement, and a long open ended tube.

All three types of containers have problems with storing the liquid drug. The liquid is transferred from the collapsible bag by suction from the cylinder when the piston is retracted. The bag needs an under pressure within to collapse properly which causes gas bubble formation within the bag. To minimize and/or eliminate this problem, a dip tube and overfilling of the bag is needed to prevent the gas in the bubble entering the cylinder. The long tube system also requires an under pressure to work and requires an open end to allow air flowing in to balance the pressure. Evaporation can take place from this open end. The spring/piston/cylinder arrangement has an over pressure to eliminate gas bubbles, but can lead to liquid leakage via the nozzle of the inhaler.

All three types or systems need to be sealed in vapour proof canisters during storage or shell life to minimize drug evaporation or evaporation of any other component, e.g. the solvent. Prior to use the container needs to be inserted into the inhaler where a hole is pierced to allow air flowing in, and to be connected to the cylinder via a rupturable sealed connector. During use which may last up to three months some evaporation always takes place, because the container is permanently connected through the cylinder and open nozzle. Evaporation can take place from the nozzle and through the walls of the container and venting hole in a canister surrounding the container. Because of stability issues, only a few types of plastic may be used to make the container for any one drug solution. It is often difficult to find a material which is stable and has a low vapour transmission rate. This problem is much worse for volatile liquids such as ethanol based solutions.

Another problem with the above inhaler and container types is that the inhaler need to be primed (operated to fill the pump and fluidic connections with liquid), wherein often up to six puffs (operations) are needed until a full dose of liquid is delivered.

The present invention relates in particular to a cartridge (reservoir) for an inhaler for dispensing liquid by means of a pump, in particular of a piston/cylinder arrangement, and/or preferably a gas-free metered dose inhaler and/or an active inhaler.

The present invention relates in particular to active inhaler such as an inhaler sold under the brand name "Respimat" shown in WO 2007/125577 A1. The inhaler has a pre-inserted cartridge as a reservoir containing a liquid, which is to be atomized. The inhaler comprises a pressure generator (pump) with a drive spring for metering and pressurizing the liquid. A capillary tube is inserted into the cartridge to fluidically connect the cartridge permanently to the pressure generator. The cartridge does not comprise any valve for fluidically connecting the cartridge to the inhaler. The pressurized liquid is discharged via a nozzle so that the liquid is atomized and discharged as a spray or aerosol.

Object of the present invention is to provide a device, preferably an inhaler, with a preferably pre-inserted cartridge, a method for filling such a cartridge with a liquid, and a use of such a cartridge, wherein priming can be eliminated or minimized and/or wherein forming of gas bubbles can be minimized and/or wherein it can be minimized or eliminated any under pressure acting on the liquid in the cartridge when liquid is delivered from the cartridge into the device or inhaler.

The above object is achieved by a device according to claim 1, by a method according to claim 25 or by a use according to claim 28. Preferred embodiments are subject of the subclaims.

The present invention overcomes most of the problems mentioned above.

Preferably, the cartridge is pre-inserted and/or pre-connected to an associated device/inhaler and/or its pressurizing means or pump. This largely eliminates any priming puffs or operations.

According to a first preferred embodiment, the cartridge comprises:

storage means, such as a collapsible bag, bellows, long tube or piston cylinder arrangement;

a normally closed, first valve preferably connecting said storage means or container to the device, inhaler, pump cylinder or the like;

a sealed outer canister to minimize and/or eliminate any evaporation or liquid from the storage means or container; and means to pressurize the outer canister.

The valve is preferably a continuous flow aerosol valve. Such valves have a spring loaded stem which can be pushed into the valve to open the valve. These valves can be built using a variety of sealing materials and are known have very long leak-free shelf lives.

The valve stem is preferably permanently connected to the associated device, inhaler, pump means, cylinder or the like and/or via a non-return valve.

The canister may be pressurized with liquefied gases or permanent gases such air.

If the container is a long tube, the diameter is preferably between 0.5 and 6 mm and more preferably between 1 mm and 4 mm.

The invention further provides according to another aspect a best method of filling the cartridge or container and pressurize the canister as follows:

the valve and the storage means or container (tube, bag, piston or the like) are sealingly mounted by crimping or other means onto the canister. The liquid is forced into the storage means or container via the (first) valve. Because the canister is sealed, the canister is pressurized as the liquid goes in the gas or air in the canister.

The container may be over filled by a small percentage, such as 10 to 50%. This ensures that an over pressure is always present while there is liquid left.

Alternatively or additionally to the over filling, the cartridge or storage means can be filled with liquid and/or sealed under low temperature, so that the increase to room temperature leads to or supports the desired over pressure.

Because the liquid is pressurized priming of the device or inhaler or any other device is minimized. The pressure required is low and preferably between 1 and 500 kPa, in particular between 1 and 200 kPa or 1 and 100 kPa. This is to prevent liquid escaping under pressure via a nozzle of the device when the device or inhaler is cocked or activated.

In the present invention all pressure values mean the pressure over the atmosphere, i.e. the gauge pressure.

According to another preferred embodiment of the present invention, the cartridge consists of or comprises:
storage means such as a collapsible bag, bellows, long tube or piston cylinder arrangement;
a normally closed, first valve connecting said storage means or container to the associated device, inhaler, pump, device cylinder or the like;
a sealed outer canister to minimize and/or eliminate any evaporation of liquid from the storage means or container; and
a second, normally closed valve connecting an air space within the outer canister to the atmosphere.

The second valve ensures that evaporation of the contents through the walls of the storage means or container is minimized as the storage means or container or canister is only open to the atmosphere when the second valve is open.

In use, both valves are opened when the devices is cocked. The first valve allows the liquid to be sucked into the device, inhaler, pump means, device cylinder or the like, while the second valve allows air to flow into the outer canister to allow the storage means, container, bag, bellows or the like to collapse or liquid to move in the tube.

If the storage means or container is a long tube, the diameter is preferably between 0.5 and 6 mm and more preferably between 1 mm and 4 mm.

If a bellows is used, a normally closed bellows is preferably used.

The valves are preferably continuous flow aerosol valves as mentioned above. However, other valves could be used as well.

The storage means or container may be overfilled by a small percentage, such as 10 to 50%.

The storage means or container may be filled after or prior to being sealed or crimped to the outer canister.

According to a further preferred embodiment of the present invention, the cartridge comprises or consists of:
storage means such as a collapsible bag, bellows, long tube or piston cylinder arrangement;
a first valve connecting said storage means or container to an associated device, inhaler, pump means, device cylinder or the like;
a locking mechanism to lock the first valve in an open position after first cocking of the device, inhaler, pump means, device cylinder or the like; and
a sealed outer canister to minimize and/or eliminate any evaporation of liquid from the storage means or container.

The first valve is closed while the device, inhaler, pump means or cartridge is in storage and opened when the device, inhaler, pump means or the like is first cocked.

The cartridge comprises optionally a second, normally closed valve connecting—preferably only temporarily—an air space within the outer canister with the atmosphere The valves are preferably continuous flow aerosol valves as already mentioned.

Generally, the second valve may be a non-return valve, such as a duckbill, umbrella or spring loaded ball valve, which opens preferably automatically.

As already mentioned, the valve stem (of the first valve) is preferably permanently connected to the device, inhaler, pump, cylinder or the like preferably via a non-return valve.

In use, both valves are opened when the device, inhaler, pump or the like is cocked, wherein the first valve remains open after the first cocking. The first valve allows the liquid to be sucked into the device, inhaler, pump, device cylinder or the like, while the second valve allows air to flow into the outer canister to allow the storage means, bag or bellows to collapse or liquid to move in the tube. If a non-return valve is used, the valve will open when a predetermined under pressure is reached in the canister.

The second valve ensures that evaporation of the contents through the walls of the storage means or container is minimized as the storage means or container is only open to the atmosphere when the second valve is open.

In another embodiment, the liquid may be stored directly in the outer canister eliminating the need for a separate or additional storage means such an inner bag. In this case, the (first) valve may be connected to a dip tube for upright cocking. The dip tube may be of a flexible type allowing for 180 degree cocking.

The (first) valve may be used with a dip tube that may be of the 360 degree ball valve type which operates at all cocking orientations.

According to a further preferred embodiment of the present invention, the cartridge comprises or consists of:
storage means such as a metal or stainless steel or coated aluminum canister to hold liquid, in particular including a drug formulation;
a normally closed, (first) valve connecting said storage means or canister to an associated device, inhaler, pump, device cylinder or the like.

The (first) valve is preferably a continuous flow aerosol valve, as already mentioned above.

The crimp used may be a standard size crimp such as a 20 mm, 18 mm, 17 mm, 15 mm crimp or any other standard or non-standard crimp.

The (first) valve may have a dip tube connected to it in which case the device, inhaler, pump or the like must be cocked while in the upside position (mouthpiece up) or may not have a dip tube or the like in which case the device must be cocked in the upside down position (mouthpiece down).

As already mentioned, the valve may be a 360 degree type valve that has a dip tube and second entry in the valve body with ball valve for 360 degree operation in which case the device, inhaler, pump or the like may be cocked in any position.

The canister may be pressurized with liquefied gases or permanent gases such as air.

If the liquid contents are volatile such as ethanol, the contents may not need to be pressurized. However, for water-based products some pressure is preferred.

In another embodiment, the preferably un-pressurized canister—but also the pressurized canister after discharge of some liquid—may have a non-return valve or any other second valve to allow air to flow into said canister to prevent pressure reduction or under pressure in the canister as liquid contents are removed. The non-return valve or second valve may be sealed with foil to prevent evaporation during storage. Then, said foil is ruptured during the first use, stroke or cocking of the device, inhaler, pump or the like.

The present invention also provides a preferred best method of filling the storage means/container and pressurizing the canister as follows:
the (first) valve (and dip tube) are sealingly mounted by crimping or other means onto the canister. The liquid is forced into the storage means or container via the (first) valve. Because the canister is sealed, the air or any other gas in the canister is pressurized as the liquid goes in the air or gas in the canister.

Because the liquid is pressurized, priming of the device, inhaler, pump or the like can be minimized or even avoided.

As already mentioned, the pressure required is low and preferably between 1 and 500 kPa. This is to prevent liquid escaping under pressure via the nozzle when the device, inhaler or pump is cocked.

When the device, inhaler, pump or the like is cocked, the cartridge or canister may move, in particular away from a part of the device, the pump, the cylinder or the like. The bottom or base of the cartridge or canister may be or come in contact with a bottom part, case or housing of the device during said movement, whereby the valve may be opened or the valve stem may be forced into a valve body opening so that the valve opens and allows liquid to flow into the device, inhaler, pump or the like. If the valve or valve stem has a stroke less than the stroke of staid movement of the cartridge or canister or less than the stroke of the inhaler or pump or a pump piston, a second spring or any other biasing means or counter-bearing means may be used or inserted between the cartridge or canister on one hand and the bottom part, case or housing of the device, inhaler, pump or the like on the other hand.

Preferably, the valve is opened only temporarily and/or normally closed.

In a further aspect of the present invention, the valve is closed or closes automatically at the end of the cocking stroke and/or in the cocked state of the device or inhaler to prevent liquid from leaking out the cartridge and/or device/inhaler.

In the present invention, the term "cocked" has to be preferably understood in the sense that a device is set in a position ready for use or discharging the liquid or is activated.

The different embodiments, aspects and features of the present invention mentioned above and/or explained or described in the following may be realized independently from each other or in any combination thereof. The cartridge may also be claimed independently from a device/inhaler.

Devices according to the present invention are in particular inhalers, but also other spraying devices for atomizing a liquid, in particular a drug or the like. The following description focuses often on inhalers as preferred devices. However, this applies preferably also for other spraying devices or the like.

Figure 2:
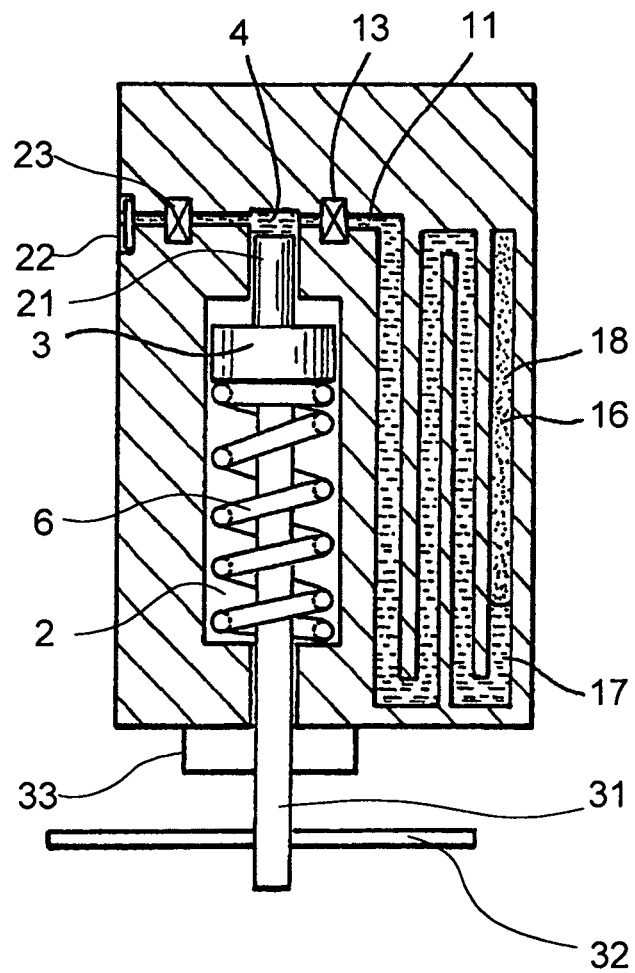
Figure 3:
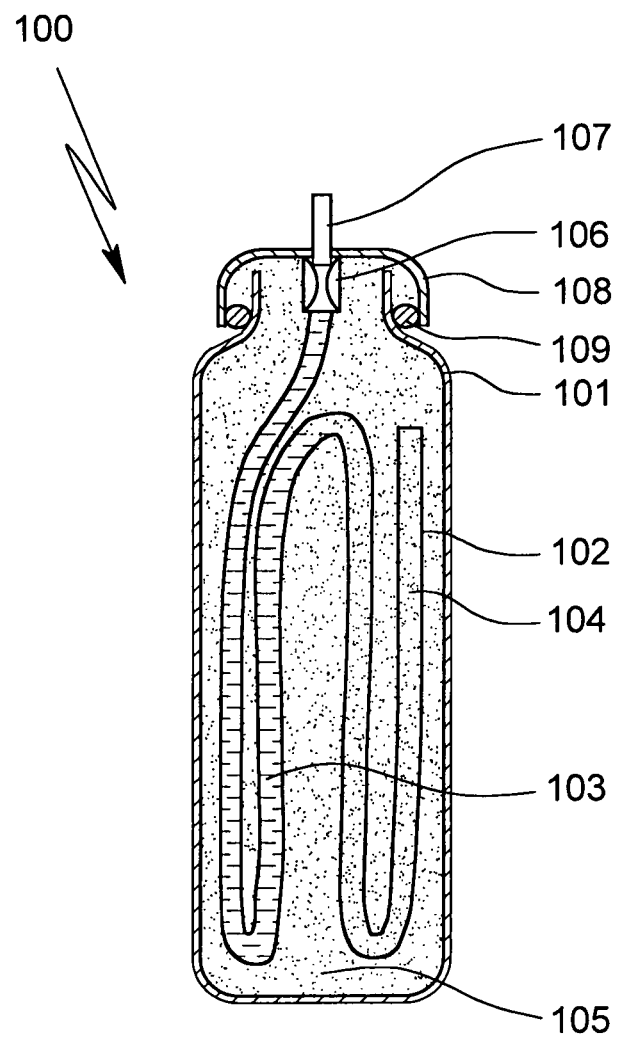
Figure 4:
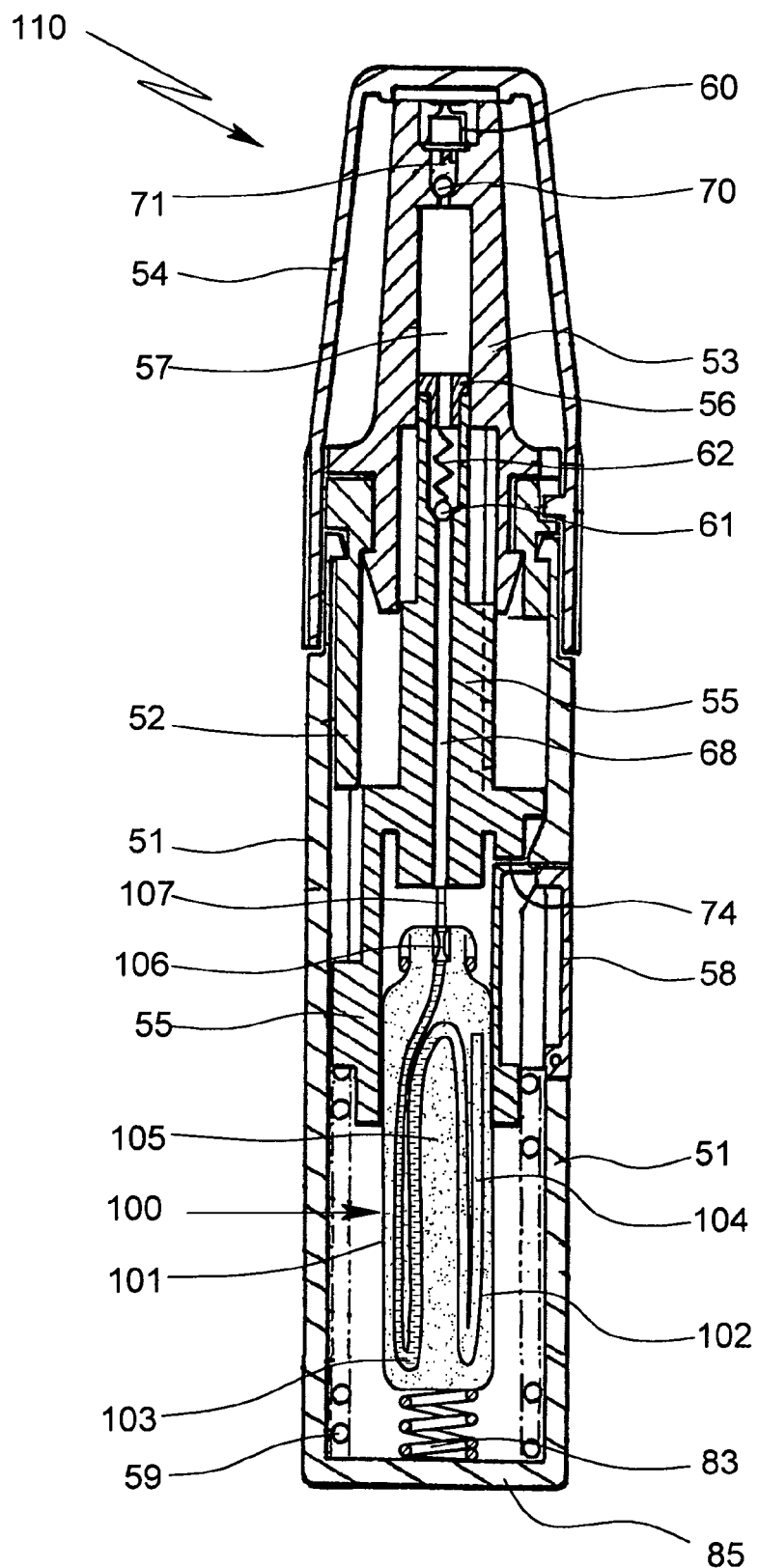
Figure 5:
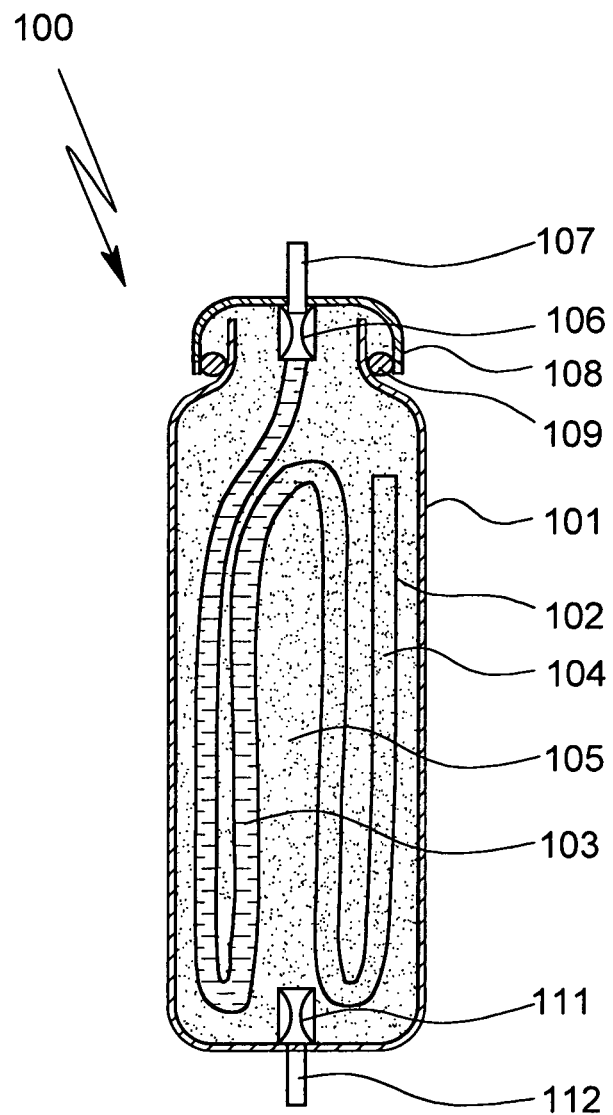
Figure 6:
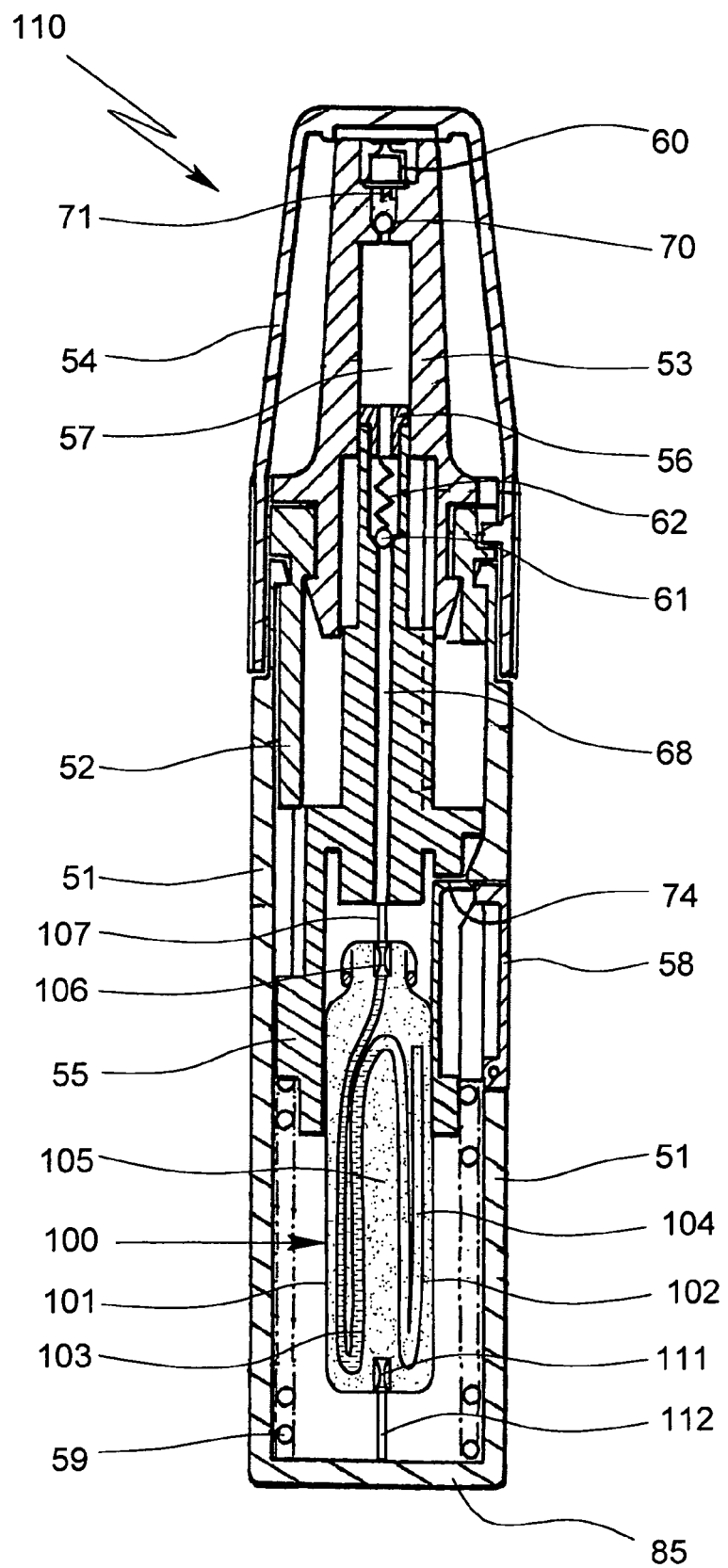
Figure 7:
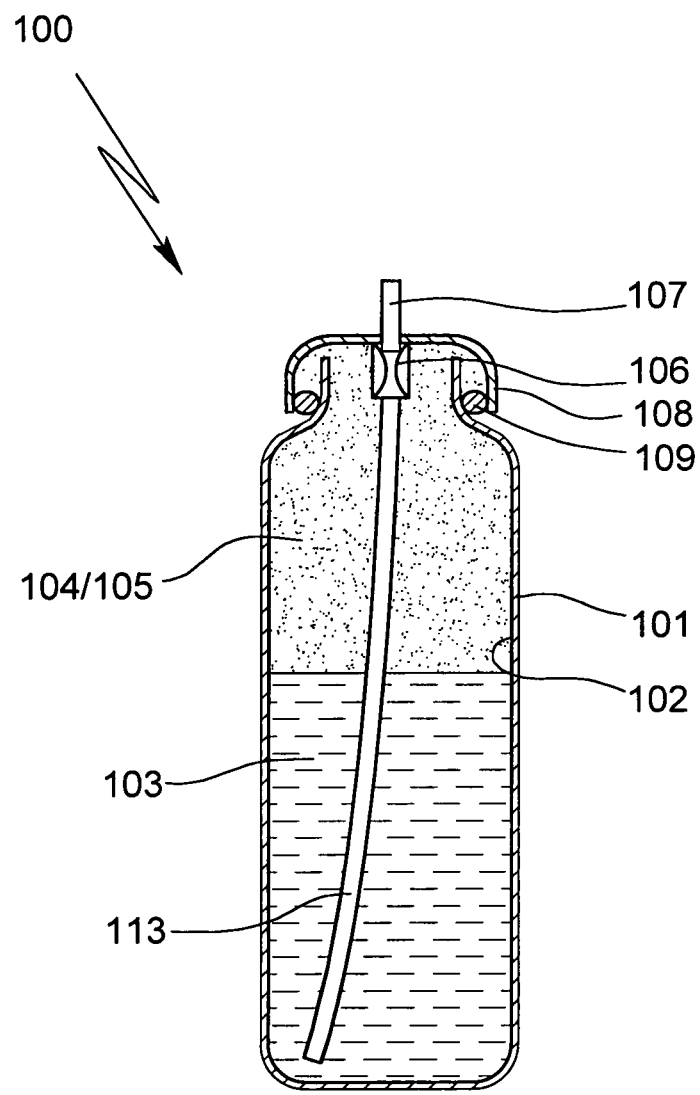
Figure 8:
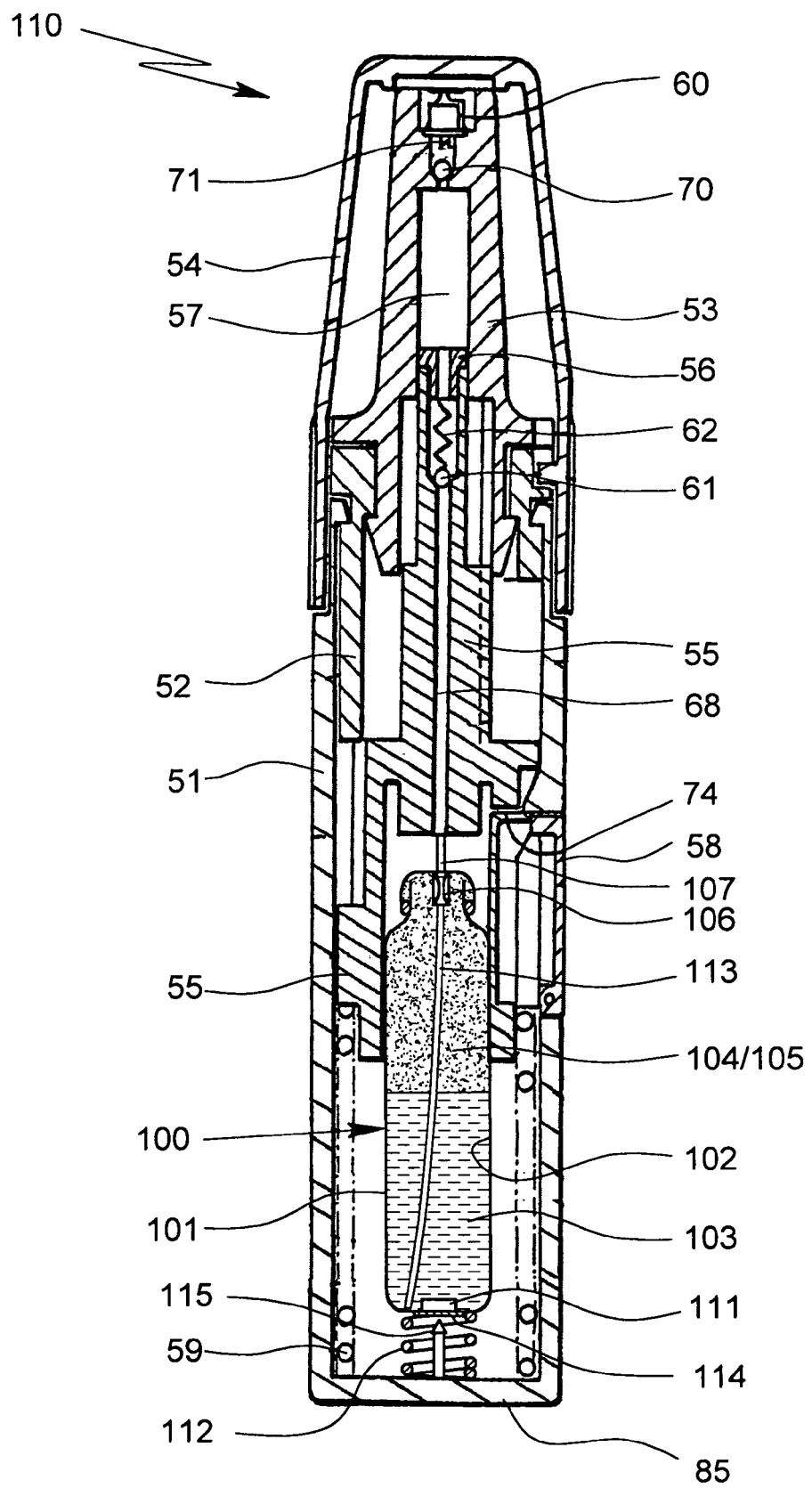
Figure 9:
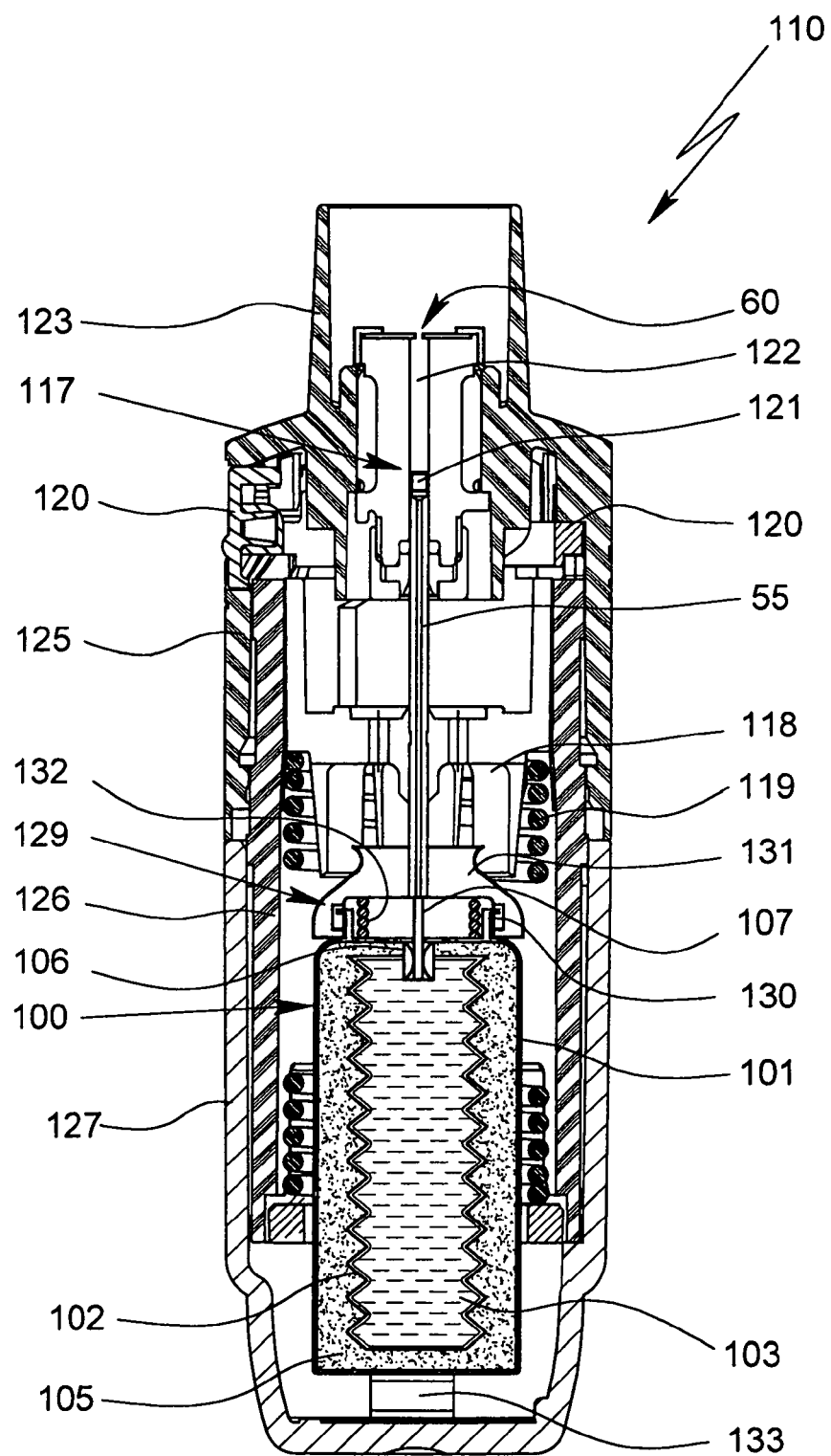
Figure 10:
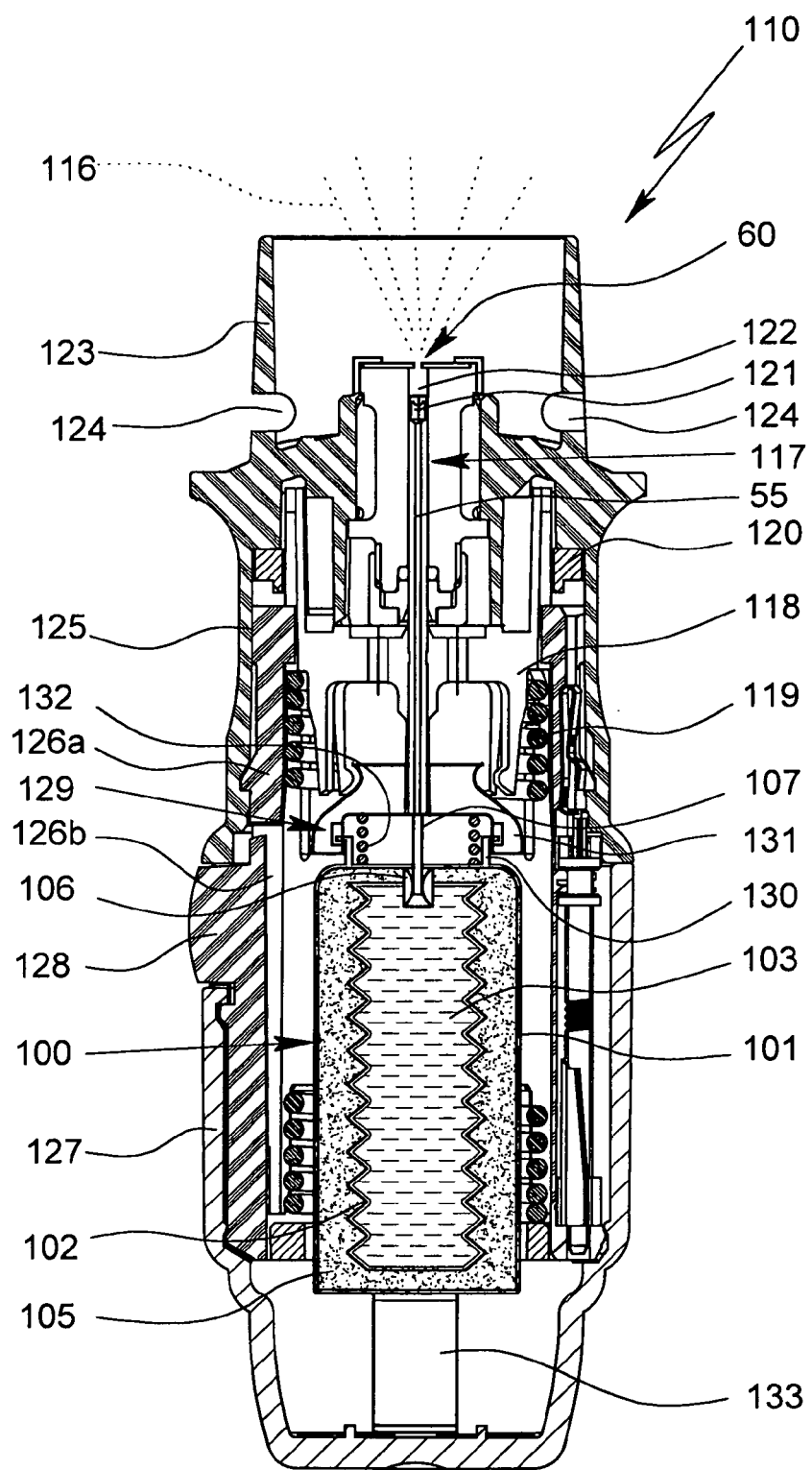

Further aspects, features, properties and advantages of the present invention are described in the claims and the subsequent description of preferred embodiments with reference to the drawing. There are shown in:

FIG. 1 a schematic section of a known inhaler;

FIG. 2 a schematic section of another known inhaler;

FIG. 3 a schematic section of a cartridge according to the present invention;

FIG. 4 a schematic section of an inhaler with the cartridge of FIG. 3 according to the present invention;

FIG. 5 a schematic section of another cartridge according to the present invention;

FIG. 6 a schematic section of an inhaler with the cartridge of FIG. 5 according to the present invention;

FIG. 7 a schematic section of a further cartridge according to the present invention;

FIG. 8 a schematic section of an inhaler with a cartridge similar to the one of FIG. 7 according to the present invention;

FIG. 9 a schematic section of another inhaler in the tensioned, activated or cocked state; and FIG. 10 a schematic section, rotated by 90° compared with FIG. 1, of the inhaler in the non-tensioned or discharged state.

In the Figures, the same reference numbers are used often for identical or similar parts, even if a repeated description is omitted. In particular identical or corresponding advantages and properties then also result or may be achieved.

FIG. 1 shows in a schematic section a metered dose spray system according to GB 2 251 898 A. The body 1 has a cavity 2 where a spring 6 and piston 21 and flange 3 are located. A cylinder 4 is formed within. The piston 21 and cylinder 4 forms a pump. A cocking and locking arrangement (of the pump) is formed by components 31, 32, 33, 34, and 35.

Liquid 10 is stored in a collapsible bag 15 within cavity 27. The liquid 10 can be sucked into the cylinder 4. Although not shown, the cavity 27 is open to the atmosphere so that the bag 15 may collapse when liquid 10 is sucked out.

The bag 10 is connected to the cylinder 4 via a tube 11 and a non-return valve 13. The valve 13 prevents back flow into the bag 15. A further non-return valve 23 prevents air being sucked into the cylinder 4 while piston 21 is retracted. During the opposite piston stroke, the liquid 10 is pressurized in the cylinder 4 and discharged via the valve 23 and a subsequent nozzle 22. The valve 23 is not needed if the atomizing nozzle 22 is small enough to prevent any back flow.

FIG. 2 shows in a schematic section another, but highly similar spray system known from GB 2 251 898 A. Here, the collapsible bag has been replaced by a long tube 16 with liquid 17 and air 18 within.

The cartridge described in the following could be used as a reservoir for a device as described in FIG. 1 or 2.

FIG. 3 shows in a schematic section a cartridge 100 according to a first embodiment of the present invention. The cartridge 100 comprises a preferably rigid and/or outer canister 101 and a storage means 102, here a long tube, within the canister 101.

The tube can have an open or a closed end.

However instead of or in addition to the tube, the storage means 102 can comprise or be formed by a bag, bellows (preferably with closed end), any cylinder piston arrangement, a rigid container, the canister 101 itself or an inliner within the canister 101 or cartridge 100 or the like.

Preferably, the storage means is arranged within the canister 101 or cartridge 100, but it can also form (partially) any outer housing or the canister 101 or the like of cartridge 100.

The storage means 102 is preferably flexible and/or collapsible. However, the storage means 102 could also be rigid or not collapsible.

The storage means 102 or tube is preferably made of plastic, foil, laminated foil, a compound or the like.

The canister 101 forms preferably an outer, rigid and/or preferably essentially cylindric housing of the cartridge 100 or storage means 102.

The storage means 102 contains liquid 103 and preferably a gas or air space 104 (here in the tube).

The cartridge 100 forms a reservoir for the liquid 103, in particular multiple doses of the liquid 103.

The liquid 103 is or contains or includes a medicament, a drug formulation or an inhalation formulation.

There is a further gas or air space 105 within the cartridge 100 or canister 101.

The gas or air in space 104 and/or 105 is preferably pressurized.

The storage means 102 or tube is connected to a (first) valve 106, which has preferably a stem 107 or any other means for operating the valve 106.

The valve 106 is sealingly mounted preferably with tap or valve cup 108 (e.g. having a diameter of 17 mm) and/or seal 109 on canister 101 and/or preferably by crimping and/or in any suitable manner.

To open the valve 106, the stem 107 is depressed or toggled sideways. When the valve 106 is open, the pressurized gas or air pushes the liquid 103 out. The valve 106 or stem 107 is preferably connected (not shown) or connectable via a connector or the like to a spray system, device, inhaler, pump, device cylinder (preferably similar to the one already described in FIGS. 1 and 2), in particular via a non-return valve (not shown).

The shown valve 106 is preferably a continuous flow aerosol valve.

Preferably, the stem 107 is biased by means of a spring (not shown) or the like into the closed position where the valve 106 is closed.

FIG. 4 shows in a schematic section an inhaler 110 or any other spray system, here also called device, with the preferably pre-inserted or installed and/or pre-connected cartridge 100 according to the present invention.

The device/inhaler 110 has a body 51 with a piston 55 with a connecting element or tube 68 (fluidically) connecting the valve 106 or valve stem 107 of the valve 106 of the cartridge 100 to a pump or cylinder 57 of the device/inhaler 110. In particular, the inhaler 110 comprises a pump—here formed by the axially moveable piston 55 and the cylinder 57—to deliver and pressurize liquid from the cartridge 100.

The piston 55 has preferably a non-return valve at its top, in particular formed by a ball 61 and, if necessary, an associated spring 62.

The piston 55 is spring-loaded by spring 59 (in FIG. 4 preferably in the upward direction). The back and forth movement of the moveable piston 55 is used to suck liquid 103 via the valve 106, stem 107, connecting element or tube 68 and/or the non-return valve into the cylinder 57 (suction stroke) and to pressurize the liquid 103 in the cylinder 57 (discharge stroke) so that the pressurized liquid is discharged via an optional second non-return valve 70, 71 connecting the cylinder 57 to an atomizing nozzle 60, in particular a mechanical break-up nozzle.

The device/inhaler 110 is shown in the cocked position with compressed spring 59 and with piston 55 fully retracted at which position the valve 106 is open.

A force produced by an optional biasing means, here a spring 83, of the device/inhaler 110 pushes the cartridge 100 or canister 101 up against the cylinder 55, connecting element or tube 68 and/or valve stem 107 so that the valve 106 is opened. In this (open) position, the liquid drug (liquid 103) can flow into the cylinder 57 forming a metering chamber. It has to be noted that the tube 68 and cylinder 57 are shown empty, i.e. without liquid 103, in FIG. 4.

When the device/inhaler 110 is fired (operated), e.g. by unlocking locking element 52—after opening or removing cover 54—the valve 106 closes as the cartridge 100 or canister 101 moves away from spring 83 or from the lower or bottom part 85 of the inhaler 110, in particular due to the discharge stroke of the piston 55 (here upwards) preferably due to the force of spring 59.

Preferably, the valve 106 is opened only temporarily and/or closing automatically.

Preferably, the valve 106 or stem 107 is permanently connected to the device/inhaler 110, connecting element or tube 68, pump (here formed by the piston 55/cylinder 57/arrangement or the like).

The biasing means (here spring 83) compensates preferably any tolerances and/or the difference between the small stroke required to open valve 106 and the larger suction and discharge stroke of the pump or inhaler 110, here piston 55. However, other constructional solutions are possible as well.

In the following, some other embodiments will be described. The previous aspects and features shall apply preferably in a similar manner and/or additionally, even if a respective description is not repeated. In particular, sometimes the same reference signs are used for the same or similar components to facilitate the understanding.

FIG. 5 shows in a schematic section a second embodiment of the cartridge 100 according to the present invention.

The cartridge 100 comprises a second valve 111 preferably with a stem 112. The second valve 111 connects the air space 105 of the cartridge 100 with the atmosphere when the valve 111 is open.

To open the valves 106 and 111, the stems 107 and 112 are depressed or toggled sideways. However, other constructional solutions are possible as well.

When the valves 106 and 111 are open, the liquid 103 can be sucked out of the storage means 102 or tube via valve 106 and air can enter into the canister 101 via valve 111. In particular, the air can replenish the air space 105 if the storage means 102 collapses due to the discharge of liquid 103. However, it is also possible that the air flowing in replenishes the air space 104 in the storage means 102 or tube, in particular if the storage means 102 is not collapsible or does not collapse. In this case the storage means 102, such as the tube, is preferably open (for example at the free end) to the air space 105 in the cartridge 100 or canister 101.

In the second embodiment, the air space 105 is preferably not pressurized.

In the second embodiment, the air space 104 is optional as it is the case in the first embodiment.

FIG. 6 shows an inhaler 110 in a schematic section similar to FIG. 4 with the cartridge 100 according to FIG. 5.

The two valves 106 and 111 may open at least essentially simultaneously and/or in the cocked position with piston 55 fully retracted. A force produced by a spring (not shown) within valve 111 pushes the canister 101 or cartridge 100 up against valve stem 107 and opens valve 106 so that the liquid 103 can flow or be sucked into the pump, here into the cylinder 57 or metering chamber of the inhaler 110.

However, the second valve 111 may open also before the first valve 106 or vice versa.

When the inhaler 110 is fired, i.e. when the piston 55 moves upwards and/or the liquid 103 is discharged, the valves 106 and 111 close as the cartridge 100/canister 101 moves away from the lower or bottom part 85 and/or from the pump, piston 55 and/or connecting element or tube 68.

FIG. 7 shows in a schematic section a third embodiment of the cartridge 100 according to the present invention. In contrast to the first and second embodiments, the storage means 102 containing the liquid 103 is formed by the preferably outer and/or rigid canister 101. The (first) valve 106 is fluidically connected to the storage means 102 preferably via a dip tube 103.

Preferably, the canister 101 is a metallic canister 101, in particular a stainless steel or coated aluminium canister 101.

The cartridge 100 or canister 101 or storage means 102 comprises a gas or air space 104/105 in particular for directly pressurizing the liquid 103.

When the valve 106 is open, the gas or air pressure pushes the liquid 103 out. In case of under pressure, the liquid 103 is sucked out by the device/inhaler 110 or its pump, here the piston/cylinder arrangement.

FIG. 8 shows an inhaler 110 in a schematic section similar to FIG. 4 and FIG. 6 with a cartridge 100 similar to the third embodiment shown in FIG. 7.

Basically, the description of FIG. 4 applies in a similar manner. However, the cartridge 100 may also form an unpressurized system or reservoir.

Preferably, the cartridge 100 comprises the second valve 111, in particular also at the free end or base or bottom of the cartridge 100 or canister 101 as in the second embodiment. Here, the second valve 111 is preferably an automatic valve and/or a non-return valve so that air can only or always enter into the cartridge 100 or canister 111 or storage means 102 when under pressure occurs when liquid 103 is sucked into the inhaler 110 or its pump (here the cylinder 57). Preferably, the valve 111 allows only gas or air to pass, but not liquid 103.

The second valve 111 opens preferably automatically when under pressure occurs.

Preferably, a seal 114 seals the valve 111 from the atmosphere during storage. This seal 114 is ruptured, preferably by a piercer 115 or the like, during the first stroke or cocking of the device/inhaler 110. However, other constructional solutions are possible as well.

FIGS. 9 and 10 show a further embodiment of an inhaler 110 according to the present invention for atomising liquid 103, particularly a highly effective pharmaceutical composition or the like, to form an aerosol 116 shown in FIG. 10.

The inhaler 110 is diagrammatically shown in a tensioned or cocked state (FIG. 9) and in a non-tensioned or discharged state (FIG. 10)

The inhaler 110 is constructed in particular as a portable inhaler and preferably operates without propellant gas. Preferably, the inhaler 110 is portable, works only mechanically and/or is hand-held.

The inhalation formulation or liquid 103 is in particular a solution, suspension or suslution (mixture of solution and suspension), but can have any form.

When the inhalation formulation or liquid 103, more particularly a pharmaceutical composition, is nebulised, the aerosol 116 is formed, which can be breathed in or inhaled by a user (not shown). Usually the inhaling is done at least once a day, more particularly several times a day, preferably at set intervals, depending on the complain from which the patient is suffering.

The inhaler 110 has in particular an insertable and preferably exchangeable cartridge 100 containing the liquid 103. The cartridge 100 thus forms a reservoir for the liquid 103, which is to be nebulised. Preferably, the cartridge 100 contains an amount of inhalation formulation or liquid 103 or active substance which is sufficient to provide up to 200 dosage units, for example, i.e. to allow up to 200 sprays or applications. A typical cartridge 100 holds a volume of about 1 to 15 ml.

The cartridge 100 is preferably substantially cylindrical or cartridge-shaped and once the inhaler 110 has been opened the cartridge 100 can be inserted therein from below and changed if desired. However, the cartridge 100 can also be pre-inserted and/or pre-connected.

Here, the cartridge 100 is preferably similar to the first embodiment. In particular, the inhalation formulation or liquid 103 is in particular held in a collapsible storage means 102, here a bellows, in the cartridge 100 or its outer canister 101. The storage means 102 is connected to the valve 106.

The canister 101 or air/gas space 105 is preferably pressurized by air or gas.

The inhaler 110 has a conveying and/or pressurizing means, such as a pump 117, for conveying, metering, pressurizing and/or discharging the inhalation formulation or liquid 103.

In the present embodiment, the inhaler 110 or pump 117 has preferably a holder 118 for the cartridge 100, an associated drive spring 119, only partly shown, with a locking element 120 which can be manually operated to release the spring 119, a conveying and/or connecting member, preferably a conveying tube or piston 55, a non-return valve 121 and/or a pump or pressure chamber 122 (similar to cylinder 57). The inhaler 110 comprises further nozzle 60, in particular a mechanical break-up nozzle, preferably in the region of a mouthpiece 123. A pre-filter (not shown) may be arranged streamup the nozzle 60.

The cartridge 100 is fixed in the inhaler 110 preferably by the holder 118. The holder 118 may be constructed so that the cartridge 100 is able to be exchanged.

Preferably, the holder 118 or piston 55 or any part or component of the inhaler 110 forms a connecting member for a fluidic connection to the cartridge 100.

As the drive spring 119 is axially tensioned the holder 118 with the cartridge 100 and the conveying tube or piston 55 is moved downwards in the drawings, the liquid 103 is sucked out of the cartridge 100 into the pressure chamber 122 of the pump 117 through the non-return valve 121. Preferably, the valve 121 is attached to or formed by the conveying tube or piston 55. Then, the inhaler 110 reaches the cocked state shown in FIG. 9.

After actuation of the locking element 120 the inhalation formulation or liquid 103 (not shown) is put under pressure in the pressure chamber 122 as the conveying tube 55 with its now closed non-return valve 121 is moved back upwards by the relaxation of the drive spring 119 and now acts as a pressing ram or piston. This pressure forces the inhalation formulation or liquid 103 through the expulsion or dispensing nozzle 60, whereupon the formulation or liquid 103 is nebulised into aerosol 116, as shown in FIG. 1.

Preferably the inhaler 110 may have a spring pressure of 5 to 200 MPa, preferably 10 to 100 MPa on the liquid 103, which is much higher than the pressure in the cartridge 100, and/or a volume of liquid delivered per stroke of 5 to 100 μl, preferably 10 to 30 μl, most preferably about 15 μl. The liquid 103 is converted into the aerosol 16, the droplets of which have an aerodynamic diameter of up to 20 μm, preferably 3 to 10 μm. The nozzle 60 has preferably a spray angle of 20° to 160°, preferably 80° to 100°.

Preferably, the liquid 103 is pre-pressurized in the cartridge 100 to a low pressure and, then, pressurized in the device/inhaler 110 or its pump 117 to a high pressure, i.e. in two stages.

Preferably, all liquid 103 is pressurized in the first stage or cartridge 100 to the first (low) pressure of preferably between 1 and 500 kPa or 1 and 200 kPa, in particular between 1 and 100 kPa. Then, only one dose of liquid 103 after the other is pressurized in the second stage or inhaler 110/pump 117 to the second (high) pressure.

It has to be noted that the cartridge 100 and/or liquid 103 are preferably propellant-free. In particular, the liquid 103 is pressurized in the cartridge 100 by gas or air pressure such that at least essentially no gas or air is outputted together with the liquid 103.

A user (not shown) can inhale the aerosol 116, while an air supply is sucked into the mouthpiece 123 through preferably at least one air supply opening 124, preferably multiple air supply openings 124. Thus, a bypass is formed so that ambient air can be sucked into the mouthpiece 123.

The inhaler 110 comprises preferably an upper housing part 125 and an inner part 126 which is rotatable relative thereto (FIG. 9) having an upper part 126a and a lower part 126b (FIG. 10), while an in particular manually operable housing part 127 is releasably fixed, particularly fitted onto the inner part 126, preferably by means of a retaining element

128. In order to insert and/or replace the cartridge 100 the housing or lower or bottom part 127 can be detached from the inhaler 110.

The cartridge 100 is preferably held by the holder 118 or mounted in the inhaler 110 such that the canister is moveable (preferably in lengthwise or axial direction and/or in direction of the back and forth movement of the pump 117 or piston/tube 55) relatively to the connecting member or holder 118 to open and close the valve 106 depending on this relative position. To achieve this relative moveability, the cartridge 100 is held preferably by a bracket-like connection 129, here between a collar 130 and a head 131, so that the relative movement is restricted, in particular to the necessary stroke of valve 106.

In the shown embodiment, the head 131 may form the connecting member for the cartridge 100 to fluidically connect it to the inhaler 110 or pump 117 and may be hald by the holder 118. Further, the head 131 may actuated the stem 107 to open and close the valve 106.

FIG. 10 shows the valve 106 in the closed state. The head 131 is spaced from the valve 106 or canister 101 as possible. However, the stem 107 or valve 106 is preferably still fluidically connected to the connecting member, head 131 or inhaler 110 in this state. This facilitates sealing. The cartridge 100 may have an optional return spring 132 biasing the head 131 into this state. However, the internal spring (not shown) of the valve 106 biasing the stem 107 in its closed position may be sufficient.

FIG. 9 shows the valve 106 in the open state. The head 131 has been moved towards the valve 106 or canister 101. The stem 107 is depressed. The optional return spring 132 is compressed. This is possible because the counter-bearing means 133 holds or biases the cartridge 100 or canister 101 against the connecting member, tube/piston 55, holder 118 or here upwards or in the axial or stroke direction so that the closing force of the valve 106 and, if spring 132 is provided, the force of spring 132 can be overcome. In this case, means 133 may be a spring 112 or the like.

The device or inhaler 110 may be constructed such that the valve 106 closes or is closed again when the end of the cocking stroke or the cocked state is reached and/or when the device or inhaler 110 is in the cocked state. In the last case, the valve 106 may close also some time after the cocked state has been reached. This closing of valve 106 is particularly preferred when the cartridge 100 or canister 101 or liquid 103 is under pressure to prevent liquid 103 from leaking out of the cartridge 100 and/or device/inhaler 110, in particular through the nozzle 60, e.g. when the inhaler 110 is not directly used after it has been cocked. In order to achieve the closing of the valve 106 even in the cocked state of the device/inhaler 110, the means 133 may be adapted to reduce its counter bearing effect or biasing force when the cocked state is reached and/or after some time. For this purpose, the means 133 may be formed by a relaxing material or by a bellows with a small venting hole or the like.

It has to be noted that other constructional solutions are possible. For example, the connecting member or head 131 can be formed by the holder 118 or tube/piston 55 or vice versa.

Preferably, a snap fit is provided to hold the valve ferrule or its stem 107 onto or within the connecting member, tube/piston 55, holder 118 or the like to prevent stem 107 coming out e.g. when inhaler 110 is dropped etc.

A large number of gasket and/or plastic materials can be used in or for the valve 106, in particular such that the materials do not react with the liquid 103. The valve stem 107 may be made of metal, i.e. aluminum or stainless steel.

The valve 106 is shown as male valve, but can be a female valve. In this case, the stem 107 can be omitted or formed by the tube 55, the connecting member, the holder 118 or any other part of the inhaler 110. Preferably, the stem 107 is not inserted into valve 106 during shelf storage or before first use or cocking of the inhaler 110.

The present invention leads to some advantages. It allows a long shelf life of the cartridge 100 and/or inhaler 110. The 1950/60's aerosol technology can be used which is very reliable and not expensive. In particular standard equipment can be used for parts, production and/or filing. Only little or no priming of the inhaler 110 is required. No evaporation takes place during the period use (after the first use or cocking) because there is no (permanent) vent. The cartridge 100 and/or inhaler 110 can be used in any desired orientation, i.e. 360 degree usage is possible.

The following filling procedures are preferred for the cartridge 100.

First Method:
1—Connect storage means 102, here bellows, to valve or mould as part off.
2—Suck all air out of valve and bellows.
3—Optional—flush valve and bellows with nitrogen etc.
4—Optional—Under cup pressurise canister 101.
5—Crimp valve/bellows (in particular cup 108) to canister 101.
6—Fill through valve 106 pressurising trapped air in air space 105. (Additional pressure if step 4 used)
7—Overfill by 10% or so to guarantee some pressure at end.

Second Method:
1—Connect storage means 102, here bellows, to valve or mould as part off.
2—Suck all air out of valve and bellows.
3—Optional—flush valve and bellows with nitrogen etc.
4—Fill through valve.
5—Overfill by 10% or so to guarantee some pressure at end.
6—Under cup pressurise canister 101.
7—Crimp valve/filled bellows (in particular cup 108) to pressurised canister.

The invention claimed is:

1. A device for dispensing or atomizing a liquid (103), such as a pharmaceutical formulation, the device comprising:
 a cartridge (100) comprising: (i) a storage means (102) in which the liquid (103) is stored under pressure, and (ii) a first valve (106), wherein the storage means (102) is connected to the first valve (106) and wherein the liquid (103) is pushed out through the first valve (106) by way of the pressure within the cartridge (100) when the first valve (106) is open; and
 a pump (117) for further pressurizing the liquid (103) downstream from the first valve (106) to convey the liquid (103) out of the device.

2. The device according to claim 1, wherein the storage means (102) is collapsible.

3. The device according to claim 1, wherein the storage means (102) is or comprises a bellows.

4. The device according to claim 1, wherein the storage means (102) comprises an outer canister (101).

5. The device according to claim 1, wherein the storage means (102) comprises a container.

6. The device according to claim 1, wherein one of the storage means (102) and the cartridge (100) comprises at least one of a gas space and an air space (104, 105) for pressurizing the liquid (103).

7. The device according to claim 1, wherein the first valve (106) is normally closed or opened only temporarily.

8. The device according to claim 1, wherein the first valve (106) closes or is closed in a cocked state of the device.

9. The device according to claim 1, wherein the first valve (106) is permanently opened, at least with or after first use or operation of the device or when priming the device.

10. The device according to claim 1, wherein at least one of:
the first valve (106) comprises a stem (107) through which the liquid (103) can be outputted and by which the first valve (106) can be opened, and
the valve (106) or stem (107) is biased into the closed position.

11. The device according to claim 1, wherein the cartridge (100) comprises a sealed outer canister (101) to minimize or eliminate any evaporation of liquid (103) from the storage means (102).

12. The device according to claim 11, wherein the pressure within the cartridge is produced by way of a pressurizing means in the canister (101).

13. The device according to claim 12, wherein the pressurizing means comprises or is formed by gas.

14. The device according to claim 11, wherein at least one of:
the cartridge (100) comprises a second valve (111) connecting a gas or air space (105) within the canister (101) to the atmosphere, and
the second valve (111) is normally closed and/or opened only temporarily.

15. The device according to claim 1, wherein the liquid (103) is pressurized in the cartridge (100) between 1 and 500 kPa.

16. The device according to claim 1, further comprising a locking mechanism to lock the first valve (106) in an open position when the device is at least one of first cocked and when the cartridge is used the first time.

17. The device according to claim 1, wherein the device is an inhaler (110).

18. The device according to claim 1, wherein the device comprises a non-return valve (121) to which the cartridge (100) is connected or connectable.

19. The device according to claim 1, wherein the pump (117) comprises a cylinder-piston-arrangement.

20. Device according to claim 1, wherein the device comprises a nozzle (60) for atomizing the pressurized liquid (103).

21. The device according to claim 13, wherein the gas is liquefied gas.

22. The device according to claim 13, wherein the gas is air.

23. The device according to claim 15, wherein the pressure of the liquid (103) is between 1 and 200 kPa.

24. The device according to claim 23, wherein the pressure of the liquid (103) is between 1 and 100 kPa.

25. The device according to claim 4 wherein the outer canister (101) is metallic.

26. The device according to claim 25, wherein the outer canister (101) is at least one of stainless steel and coated aluminum.

27. The device according to claim 5, wherein the container is selected from a tube, a bag or a piston.

28. The device according to claim 1, wherein the pump pressurizes the liquid substantially higher than the pressure within the cartridge (100).

* * * * *